United States Patent [19]

Chappell

[11] Patent Number: 5,795,344
[45] Date of Patent: Aug. 18, 1998

[54] ABSORBENT ARTICLE WITH PROTECTION CHANNEL

[75] Inventor: Charles John Chappell, Appleton, Wis.

[73] Assignee: Kimberly-Clark Worldwide, Inc., Neenah, Wis.

[21] Appl. No.: 832,595

[22] Filed: Apr. 2, 1997

Related U.S. Application Data

[60] Provisional application No. 60/035,881 Dec. 20, 1996.
[51] Int. Cl.⁶ .................................................. A61F 13/15
[52] U.S. Cl. ...................... 604/379; 605/387; 605/385.1
[58] Field of Search ........................... 604/378, 379, 604/385.1, 387

[56] References Cited

U.S. PATENT DOCUMENTS

| | | |
|---|---|---|
| 2,064,431 | 12/1936 | Jurgensen . |
| 2,787,271 | 4/1957 | Clark ................................. 604/379 |
| 3,343,543 | 9/1967 | Glassman . |
| 3,411,504 | 11/1968 | Glassman . |
| 3,430,630 | 3/1969 | Megison et al. . |
| 3,444,859 | 5/1969 | Kalwaites . |
| 3,575,174 | 4/1971 | Mogor ............................. 604/385.1 |
| 3,621,847 | 11/1971 | Roberson . |
| 3,736,931 | 6/1973 | Glassman ........................ 604/385.1 |
| 4,059,114 | 11/1977 | Richards . |
| 4,079,739 | 3/1978 | Whitehead . |
| 4,184,498 | 1/1980 | Franco . |
| 4,458,468 | 7/1984 | Sivilich ................................ 53/428 |
| 4,526,825 | 7/1985 | Whitehead ............................. 428/74 |
| 4,624,666 | 11/1986 | De Rossett et al. ............. 604/379 X |
| 4,655,759 | 4/1987 | Romans-Hess et al. ......... 604/385 R |
| 4,678,464 | 7/1987 | Holtman ........................... 604/385.1 |
| 4,781,710 | 11/1988 | Megison et al. ............... 604/385.1 X |
| 4,790,838 | 12/1988 | Pigneul et al. ........................ 604/366 |
| 4,795,455 | 1/1989 | Luceri et al. ......................... 604/386 |
| 5,030,229 | 7/1991 | Yang ................................. 604/385.1 |
| 5,053,029 | 10/1991 | Yang ................................. 604/385.1 |
| 5,104,396 | 4/1992 | Oatley et al. ........................ 604/379 |
| 5,151,091 | 9/1992 | Glaug et al. ...................... 604/385.1 |
| 5,171,302 | 12/1992 | Buell ................................. 604/385.1 |
| 5,197,959 | 3/1993 | Buell ................................. 604/385.1 |
| 5,211,641 | 5/1993 | Roos et al. ....................... 604/385.1 |
| 5,300,055 | 4/1994 | Buell ................................. 604/385.1 |
| 5,312,386 | 5/1994 | Correa et al. .................. 604/385.1 X |
| 5,366,453 | 11/1994 | Zehner et al. .................... 604/385.2 |
| 5,399,175 | 3/1995 | Glaug et al. ...................... 604/385.1 |
| 5,423,786 | 6/1995 | Fung et al. .......................... 604/367 |
| 5,500,068 | 3/1996 | Srinivasan et al. .................... 156/148 |
| 5,505,720 | 4/1996 | Walters et al. ....................... 604/378 |
| 5,514,104 | 5/1996 | Cole et al. ............................ 604/366 |
| 5,674,341 | 10/1997 | Ng ..................................... 604/387 |

FOREIGN PATENT DOCUMENTS

| | | |
|---|---|---|
| 0 597 273 A1 | 5/1994 | European Pat. Off. . |
| 2 258 403 | 2/1993 | United Kingdom . |
| WO 96/23474 A1 | 8/1996 | WIPO . |

*Primary Examiner*—Mary Beth Jones
*Attorney, Agent, or Firm*—Thomas J. Connelly

[57] ABSTRACT

An absorbent article such as a sanitary napkin has a cover, a baffle and an absorbent between the cover and baffle and includes an embossed channel in the absorbent. The channel is positioned inward from the absorbent edge. The channel impedes the flow of fluid toward the edges of the absorbent article and increases absorbent utilization in the absorbent article.

24 Claims, 1 Drawing Sheet

ABSORBENT ARTICLE WITH PROTECTION CHANNEL

The application claims priority from the U.S. Provisional application Ser. No. 60/035,881 filed Dec. 20, 1996, the disclosure of which is incorporated herein by reference.

FIELD OF THE INVENTION

The present invention relates to a disposable absorbent article, and more particularly, to a sanitary napkin having a fluid impeding barrier. Most particularly, the invention relates to a sanitary napkin having an embossed channel positioned inward from the absorbent edge which provides a fluid impeding barrier.

BACKGROUND OF THE INVENTION

All manner and variety of devices or appliances are configured for absorption of body fluids, such as blood and menses, are well known. Sanitary napkins are the most frequently used of these devices. The prior art is replete with patents relating to protective pads and sanitary napkins for the absorption of body fluids and protecting the undergarment from staining. While such sanitary napkins have a function of protecting the undergarment, they are deficient in one primary area of performance. The absorbent in the sanitary napkins draws fluid toward the edge of the pad, increasing the likelihood of failure by allowing leakage of the body fluid off the pad and onto the wearer's clothes.

The effect of fluid runoff is apparent in all forms of sanitary napkins including those having increased absorbency and designed for heavy flow. It has been suggested that from 20-25 percent of all sanitary napkins leak. There have been several attempts in the feminine care art to minimize the undesirable side leakage problem associated with the use of sanitary napkins. Such efforts have tended to focus on incorporating into the absorbent structure high molecular weight absorbent materials, such as superabsorbents, which can swell from a small particle size into a much larger size with the absorption of fluids.

Others have used fluid impermeable barriers designed to halt the flow of body fluid at the edge of the absorbent. Such barriers typically are positioned adjacent to the edge of the absorbent so any fluid that migrates to the edge of the absorbent is stopped by the barrier. Generally, such barriers are stiff and uncomfortable to the wearer.

Others have utilized a fluid-impermeable channel extending along the longitudinal axis of the sanitary napkin. The channel is designed to distribute the body fluid along the length of the absorbent. Desirably, the longitudinal channel prevents a radial spreading of any fluid toward the longitudinal edge of the absorbent. This radial fluid absorption has generally been associated with incidents or occurrence of leakage. While several barriers have been taught by the prior art, there still exists a need to wick fluid away from the point of insult, effectively utilize a greater amount of the absorbent capacity of the sanitary napkin and simultaneously prohibit or impede fluid from flowing toward the edge of the sanitary napkin.

SUMMARY OF THE INVENTION

Briefly, the present invention is an absorbent article, illustratively described herein as a sanitary napkin, having a fluid permeable cover, a liquid-impermeable baffle, and an absorbent positioned between the cover and the baffle. The sanitary napkin includes an embossed fluid impeding channel positioned inward from the edge of the absorbent. Desirably the embossed channel has a thickness of about 10 percent to about 50 percent relative to the uncompressed thickness of the sanitary napkin.

It is an object of the invention to provide an absorbent having an embossed channel positioned inward from the absorbent edge which impedes the flow of fluid from the central portion of the sanitary napkin to the edge of the sanitary napkin.

It is another object of the invention to provide a sanitary napkin wherein the absorbent at the center of the sanitary napkin has a density that is different from the absorbent density at the edge.

BRIEF DESCRIPTION OF THE DRAWINGS

The invention will be further described in conjunction with the accompanying drawings wherein.

DETAILED DESCRIPTION OF THE PREFERRED EMBODIMENTS

Figure 1:
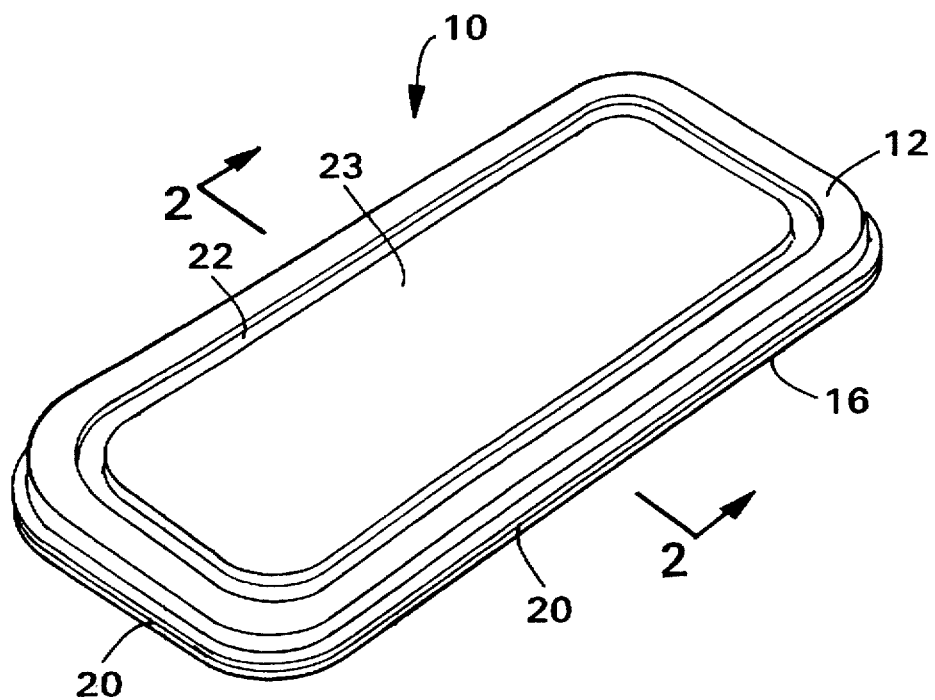
FIG. 1 is a top plan view of one embodiment of the absorbent article of the present invention.
Figure 2:
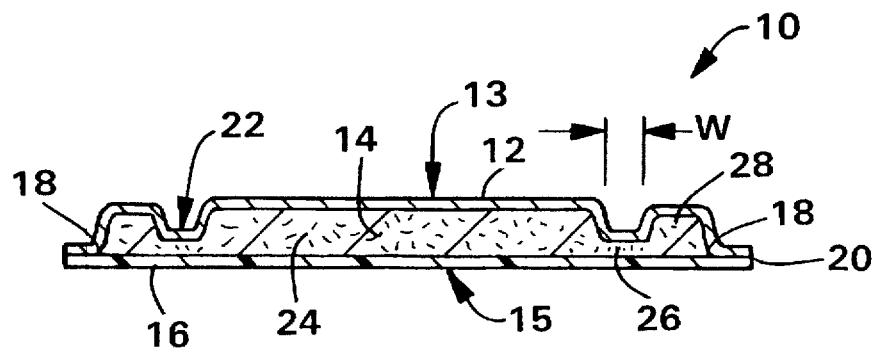
FIG. 2 is a cross-sectional view of FIG. 1 along lines 2—2.
Figure 3:
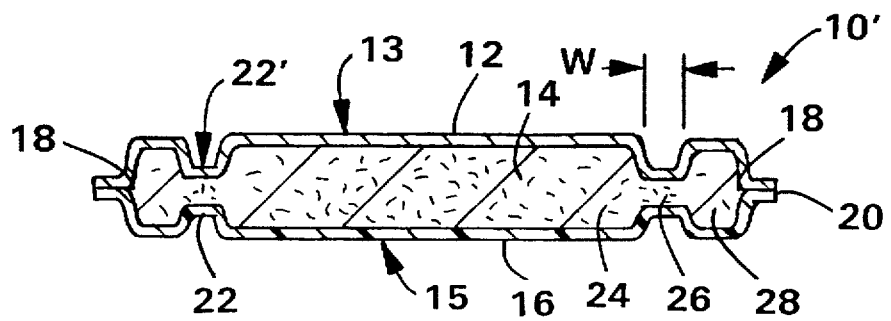
FIG. 3 is a cross-sectional view of an alternative embodiment of the present invention.

Referring particularly to FIGS. 1–3 of the drawings, in which like parts are identified with like reference numerals, FIG. 1 illustrates a top view of a sanitary napkin 10. As viewed from the top, i.e., that side which would normally be placed adjacent to the wearer during use, the sanitary napkin 10 is comprised of three layers of material. The top layer comprises a fluid permeable cover 12 having a body facing surface 13; an absorbent middle layer 14 which can be shorter and narrower than the cover 12; and a liquid-impervious bottom layer or baffle 16 having a garment facing surface 15. As seen in FIG. 2, the cover 12 and baffle 16 extend beyond an edge 18 of the absorbent 14 and are sealed together. The sealed cover 12 and baffle 16 enclose the absorbent 14 and define a perimeter 20 of the sanitary napkin 10. As used herein "edge" or "edge of the absorbent" are equivalent and encompasses the border at which the absorbent 14 terminates, without limitation to the longitudinal sides or the transverse ends of the absorbent 14 unless specifically so stated. Alternatively, the cover 12, absorbent 14 and baffle 16 can have a coterminous edge, not shown, but this is not preferred. The cover 12 and the baffle 16 may be sealed together using any suitable means that will not leave a hard, uncomfortable residue that may be annoying to the wearer. As used herein, the term "sealed" also encompasses configurations whereby the cover 12 is joined to the baffle 16 by affixing the cover 12 to an intermediate member, not shown, which may in turn be affixed to the baffle 16. Methods for attaching the cover 12 and the baffle 16 are well known to those skilled in the art and include the use of hot melt adhesive, pressure sensitive adhesive, construction adhesive, double-sided tape, heat sealing and ultrasonic bonding.

As used herein, the term "sanitary napkin" refers to an article which is worn by females adjacent to the pudendal region and which is intended to absorb and contain various exudates which are discharged from the body such as blood, menses, and urine, and which is intended to be discarded when soiled, not laundered and reused. Interlabial devices which reside partially within and partially external of the female wearer's vestibule are also within the scope of this invention.

Referring to FIG. 2, the sanitary napkin 10 further includes a fluid impeding channel 22 that is embossed into the sanitary napkin 10. The channel 22 is embossed into at least two of the layers of the sanitary napkin 10. As seen in FIG. 2, the channel 22 is embossed into the absorbent 14 from at least one of the two outer surfaces, that is, from the body facing surface 13, so that the channel 22 is embossed into both the cover 12 and the absorbent 14. Optionally, the channel 22 can be embossed into the garment-facing surface 15 and absorbent 14, not shown. Referring to FIG. 3 the fluid impeding channel 22' is embossed into all three layers of the sanitary napkin 10' so that the channel 22 resides in the body facing surface 13, the garment-facing surface 15 and the absorbent 14 of the sanitary napkin 10'.

Since the channels 22 and 22' are similar only one will be described except where otherwise specifically stated. Looking at the sanitary napkin 10 in greater detail, the sanitary napkin 10 is illustrated as having a racetrack shape, but is not limited thereto. The sanitary napkin 10 can have an hourglass, oval or any other shape or configuration that will allow the sanitary napkin 10 to come into intimate contact with the wearer.

The sanitary napkin 10 of the present invention may be any thickness and may be designed for absorbing light fluid flows to heavy fluid flows and including surge flows. Accordingly, the channel 22 of the present invention is suitable for a thin pad which can have a thickness of a few millimeters to a relatively thick pad having a thickness of about 15 millimeters.

The cover 12 is designed to contact the body of the wearer and therefore should be easily penetrated by body fluids. The cover 12 should also be non-irritating to the wearer's skin and preferably, will not absorb an appreciable amount of fluid insulting its surface. The cover 12 can be constructed of a woven or nonwoven, natural or synthetic material. Suitable materials include bonded carded webs of polyester, polypropylene, polyethylene, nylon, or other heat-bondable fibers. Other polyolefins, such as copolymers of polypropylene and polyethylene, linear low-density polyethylene, finely-perforated film webs and net material, also work well. Particularly preferred are composite materials of a polymer and a nonwoven fabric material. Still another cover material is a spunbond web of polypropylene. The web can contain about 1% to about 6% titanium dioxide pigment to give it a clean, white appearance. A uniform spunbond material is desirable because it has sufficient strength in the longitudinal direction, even after being perforated, to resist being torn or pulled apart during use. The most preferred polypropylene webs have a weight of between about 18 and 40 grams per square meter. An optimum weight is between about 30 and about 40 grams per square meter.

To aid in the penetration of the liquid through the web, the cover 12 can also be treated with a surfactant to improve its hydrophilic characteristics. The surfactant can include topical additions or internally applied materials like polysiloxanes.

The absorbent 14 is positioned between the cover 12 and the baffle 16. The materials utilized for the absorbent 14 are designed to absorb body exudates, including menstrual fluids, blood and urine. Suitable materials include wood pulp fluff, rayon, cotton and meltblown polymer, such as polyester, polypropylene or coform. Coform is an air-formed combination of meltblown polymers, such as polypropylene, and absorbent staple fibers, such as cellulose. A preferred material is wood fluff, for it is low in cost, relatively easy to form and has good absorbency. The absorbent 14 may be a composite comprised of a hydrophilic material that can be formed from various natural or synthetic fibers, wood pulp fibers, regenerated cellulose or cotton fibers, an airlaid tissue or a blend of pulp and other fibers. The absorbent 14 can be made from other well known materials used in absorbent articles, including multiple layers of cellulose wadding, rayon fibers, cellulose sponge, hydrophilic synthetic sponge, such as polyurethane, and the like. The capacity of the absorbent 14 may be varied depending upon the intended usage of the final product.

The baffle 16 acts as a barrier between the absorbed body fluids contained in the absorbent 14 and the person's undergarment. The baffle 16 should be nonabsorbent and impervious to liquids. The baffle 16 should be soft and compliant since a portion of the baffle 16 may reside adjacent the thigh region of the wearer. As used herein, the term "compliant" refers to materials which will readily conform to the general external shape and contours of the human anatomy. In a preferred embodiment, the baffle 16 may permit the passage of air or vapor out of the sanitary napkin 10 while blocking the passage of liquids from the absorbent 14. A good material for the baffle 16 is a microembossed, polymeric film, such as polyethylene or polypropylene having a thickness in the range of from about 0.012 mm to about 1.0 mm. Bicomponent films can also be used as well as woven and nonwoven fabrics which have been treated to render them liquid-impermeable.

The sanitary napkin 10 can further include one or more additional layers, not shown, that are designed to enhance, modify or transfer fluid in a preferential manner. Such layers include cellulosic and polymeric materials such as tissue, superabsorbents and melt blown materials. Such layers and materials are commercially available from several sources and are well known to those skill in construction of disposable absorbent articles, such as sanitary napkins, diapers and incontinent devices. The sanitary napkin 10 can also include shape conforming members, not shown, which are adapted to contort and/or conform the sanitary napkin 10 to a wearer's anatomy during use.

As is customary in the art, the sanitary napkin 10 can further include an adhesive, not shown, positioned on the garment-facing surface 15. The adhesive is typically covered by a peel strip to protect the adhesive until the user removes the protective strip in preparation for placement and use of the sanitary napkin 10.

The embossed channel 22 is positioned inward from the edge 18 of the absorbent 14 to define at least three distinguishable portions of the absorbent 14: an inner portion 24, a channel portion 26 and an outer portion 28. As used herein the terms "inward" or "inner" are used to describe a locus or direction as toward the center 23 of the sanitary napkin 10, as seen in FIG. 1. The center 23 can be a single point that corresponds to the intersection of a longitudinal central axis and a transverse central axis of the sanitary napkin 10. Desirably, the channel 22 is positioned inward relative to the edge 18 by a distance of from about 0.5 millimeters to about 20 millimeters and completely encircles the inner portion 24 of the absorbent 14. More desirably, the channel 22 follows the general contour of the absorbent 14 and is positioned inward from the edge 18 from about 3 millimeters to about 10 millimeters. One skilled in the art will recognize that the channel 22 can be asymmetrically positioned on the absorbent 14 relative to the longitudinal sides or transverse ends so that portions of the channel 22 may reside closer to the sides than the ends or vice versa.

The channel 22 can be formed by compressing a portion of the body facing surface 13, a portion of the garment facing surface 15 (not shown) or a portion of both the body facing surface 13 and the garment facing surface 15, as seen in FIG. 3. Desirably, the compression of the body facing surface 13, garment facing surface 15 or both is sufficient to retain the cover 12, baffle 16 or both, respectively, adjacent to the absorbent channel portion 26. It is critical to the invention that the absorbent of the channel portion 26 have a greater density than the absorbent 14 in either of the inner portion 24 or outer portion 28. It is an important aspect of the invention that the absorbent 14 of the channel portion 26 be compressed or densified only to the extent that the channel portion 26 impedes or slows but does not halt the movement of fluid through the densified absorbent 14. The embossed channel 22 of the present invention is designed to reduce leakage by channeling body fluids away from the edge 18 of the absorbent 14 and toward non-utilized or under utilized areas of the absorbent 14. Preferably, in forming the embossed channel 22, the channel portion 26 of the absorbent 14 is compressed to about 10 percent to about 60 percent of the uncompressed thickness. Desirably, the absorbent 14 is compressed to about 15 percent to about 50 percent and more desirably from about 20 percent to about 45 percent of the uncompressed thickness. Alternatively, the density of the absorbent 14 in the channel portion 26 should be from about 0.10 grams/cubic centimeter (g/cc) to about 0.25 g/cc. Preferably the density of the absorbent 14 in the channel portion 26 is from about 0.15 g/cc to about 0.25 g/cc and more preferably from about 0.17 g/cc to about 0.20 g/cc. The density of the absorbent 14 in the inner portion 24 and outer portion 28 can, independently, range from about 0.05 g/cc to about 0.10 g/cc. Desirably, the density of the absorbent 14 in the inner portion 24 is greater than the density of the absorbent 14 in the outer portion 28. Surprisingly, by compressing the absorbent 14 as described to form the embossed channel 22 a greater utilization of the absorbent 14 can be achieved. Advantageously, when the density of the absorbent 14 in the inner portion 24 is greater than the density of the absorbent in the outer portion 28, fluid wicked along the channel 22 will preferentially desorb into the inner portion absorbent 24, thus reducing the likelihood of fluid moving to the edge 18 of the absorbent 14. Moreover, relative to an occlusive channel or barrier, the product is less irritating to the user when worn.

The channel 22 may be produced in any manner well known in the art, such as by application of heat, including hot calendar embossing or by using ultrasonic means. The width, "W" of the embossed channel 22 should be such that the sanitary napkin 10 is not cut during the embossing nor so wide so as to allow the fluid to gather and pool in the channel 22. Preferably, the width, "W" of the embossed channel 22 may range from about 0.5 millimeters to about 10 millimeters. More preferably, the width, "W" of the channel 22 is from about 1 millimeter to about 5 millimeters.

The present invention will be illustrated by the following examples, which are not to be construed in any way as imposing limitations upon the scope of the invention described herein.

EXAMPLES 1–6

In each of the examples a sheet of coform was used having a pulp-to-polymer weight % compositional ratio of about 70/30. Each sheet had a length of 170 millimeters and a width of 90 millimeters. The sheet was visually divided substantially in half into side A and side B. Side A was then densified by pneumatically compressing the entire surface of side A for approximately ten seconds to the specified density. The center of the sheet was insulted with a blue dye/water solution at a rate of about 2.3 milliliters per minute for a time period of about one minute. After about one minute side A and side B were physically separated using a rotary knife and the amount of absorbed fluid was determined using techniques known in the art. The results appear in Table 1 below.

TABLE 1

| Sample | Density of Absorbent (grams/cc) | | Fluid Absorbed (weight %) | |
| --- | --- | --- | --- | --- |
| | A | B | A | B |
| 1 | 0.17 | 0.09 | 69 | 31 |
| 2 | 0.15 | 0.08 | 69 | 31 |
| 3 | 0.14 | 0.09 | 71 | 29 |
| 4 | 0.18 | 0.09 | 64 | 36 |
| 5 | 0.16 | 0.09 | 59 | 41 |
| 6 | 0.15 | 0.08 | 63 | 37 |

The above examples illustrate that a channel in an absorbent article having an absorbent with density that is greater than the adjacent absorbent will preferentially absorb and move fluid along the channel.

While the invention has been described with reference to several preferred embodiments and illustrated with regard to a range of optional features, those skilled in the art will appreciate that various substitutions, omissions, modifications, and changes may be made without departing from the spirit hereof. Accordingly, it is intended that the foregoing description be deemed exemplary of the preferred scope of the present invention and not deemed a limitation thereof.

I claim:

1. An absorbent article comprising:
   a. an absorbent; and
   b. a channel positioned inward from and along at least a portion of an edge of said absorbent, said channel substantially defining in said absorbent an inner portion and an outer portion, wherein the density of said absorbent in said inner portion is greater than the density of said absorbent in said outer portion.

2. The absorbent article of claim 1 wherein said channel has a width of from about 0.5 millimeters to about 10 millimeters.

3. The absorbent article of claim 1 wherein said width of said channel is about 1 millimeter to about 5 millimeters.

4. The absorbent article of claim 2 wherein said channel is positioned inward from said edge a distance of from about 0.5 millimeters to about 20 millimeters.

5. The absorbent article of claim 4 wherein said channel is positioned inward from said edge a distance of from about 3 millimeters to about 10 millimeters.

6. The absorbent article of claim 1 wherein said absorbent in said channel portion has a density greater than a density of said absorbent in either of said inner portion or said outer portion.

7. The absorbent article of claim 6 wherein the density of said absorbent in said channel portion is from about 0.10 g/cc to about 0.25 g/cc.

8. The absorbent article of claim 6 wherein the density of said absorbent in said channel portion is from about 0.15 g/cc to about 0.25 g/cc.

9. The absorbent article of claim 6 wherein the density of said absorbent in said channel portion is from about 0.17 g/cc to about 0.20 g/cc.

10. The absorbent article of claim 6 wherein the density of said absorbent in said inner portion and said outer portion independently ranges from about 0.05 g/cc to about 0.1 g/cc.

11. An absorbent article comprising:
  a. a fluid-permeable cover;
  b. a liquid-permeable baffle;
  c. an absorbent positioned between said cover and said baffle; and
  d. an embossed fluid-impeding channel positioned inward from and along at least a portion of an edge of said absorbent, said embossed channel substantially defining in said absorbent an inner portion, a channel portion and an outer portion, wherein the density of said absorbent in said inner portion is greater than the density of said absorbent in said outer portion.

12. An absorbent article comprising:
  a. a fluid-permeable cover having a body facing surface;
  b. a liquid-impermeable baffle having a garment facing surface;
  c. an absorbent positioned between said cover and said baffle; and
  d. an embossed fluid-impeding channel in said absorbent and at least one of said facing surfaces, said fluid-impeding channel being positioned inward from and along at least a portion of an edge of said absorbent and substantially defining in said absorbent an inner portion, a channel portion and an outer portion and wherein said absorbent in said channel portion has a density greater than a density of said absorbent in either of said inner portion or said outer portion and said absorbent in said outer portion has a density less than the density of said absorbent in said inner portion.

13. The absorbent article of claim 12 wherein said fluid-impeding channel is embossed into said absorbent and said body facing surface.

14. The absorbent article of claim 12 wherein said fluid-impeding channel is embossed into said absorbent and said garment facing surface.

15. The absorbent article of claim 12 wherein said fluid-impeding channel is embossed into said absorbent, said body facing surface and said garment facing surface.

16. The absorbent article of claim 12 wherein said absorbent in said channel portion has a density of from about 0.15 g/cc to about 0.25 g/cc.

17. The absorbent article of claim 12 wherein said absorbent in said inner portion has a density of from about 0.05 g/cc to about 0.1 g/cc.

18. The absorbent article of claim 12 wherein said embossed channel has a width of from about 0.5 millimeters to about 10 millimeters.

19. The absorbent article of claim 12 wherein said width of said channel is about 1 millimeter to about 5 millimeters.

20. The absorbent article of claim 12 wherein said channel is positioned inward from said edge of said absorbent a distance of from about 0.5 millimeters to about 20 millimeters.

21. The absorbent article of claim 12 wherein said channel is positioned inward from said edge of said absorbent a distance of from about 3 millimeters to about 10 millimeters.

22. A sanitary napkin comprising:
  a. a fluid-permeable cover having a body facing surface;
  b. a liquid-impermeable baffle having a garment facing surface;
  c. an absorbent positioned between said cover and said baffle, wherein said cover and said baffle extend beyond an edge of the absorbent to enclose said absorbent; and
  d. an embossed fluid-impeding channel in said absorbent and at least one of said facing surfaces, said fluid-impeding channel being positioned inward from and along at least a portion of an edge of said absorbent by a distance of from about 0.5 millimeters to about 20 millimeters and substantially defining in said absorbent an inner portion, a channel portion and an outer portion and wherein said absorbent in said channel portion has a density greater than a density of said absorbent in either of said inner portion or said outer portion and said absorbent in said inner portion has a density greater than the density of said absorbent in said outer portion.

23. The sanitary napkin of claim 22 wherein the density of said absorbent in said channel portion is from about 0.15 g/cc to about 0.25 g/cc.

24. The absorbent article of claim 22 wherein said fluid-impeding channel is embossed into said absorbent and said body facing surface.

* * * * *

UNITED STATES PATENT AND TRADEMARK OFFICE
CERTIFICATE OF CORRECTION

PATENT NO. : 5,795,344
DATED : August 18, 1998
INVENTOR(S) : Charles John Chappell It is certified that error appears in the above-identified patent and that said Letters Patent is hereby corrected as shown below:

Claim 11, column 7, line 3, delete "liquid-permeable" and substitute therefor --liquid-impermeable--.

Signed and Sealed this

Twenty-third Day of November, 1999

*Attest:*

Q. TODD DICKINSON

*Attesting Officer*           *Acting Commissioner of Patents and Trademarks*